(12) United States Patent
Wyeth

(10) Patent No.: US 10,786,722 B2
(45) Date of Patent: Sep. 29, 2020

(54) APPARATUS AND METHOD FOR REPETITIVE TRAINING OF GOLF SWING

(71) Applicant: Martin Wyeth, Ponte Vedra, FL (US)

(72) Inventor: Martin Wyeth, Ponte Vedra, FL (US)

( * ) Notice: Subject to any disclaimer, the term of this patent is extended or adjusted under 35 U.S.C. 154(b) by 39 days.

(21) Appl. No.: 16/155,490

(22) Filed: Oct. 9, 2018

(65) Prior Publication Data

US 2019/0105547 A1 Apr. 11, 2019

Related U.S. Application Data

(60) Provisional application No. 62/569,890, filed on Oct. 9, 2017.

(51) Int. Cl.
| | | |
|---|---|---|
| A63F 9/24 | (2006.01) | |
| A63B 69/36 | (2006.01) | |
| A63B 24/00 | (2006.01) | |
| A61B 5/00 | (2006.01) | |
| A63B 71/06 | (2006.01) | |
| A63B 60/46 | (2015.01) | |
| A61B 5/11 | (2006.01) | |
| A63B 102/32 | (2015.01) | |

(52) U.S. Cl.
CPC ........ *A63B 69/3658* (2013.01); *A61B 5/1124* (2013.01); *A61B 5/6895* (2013.01); *A63B 24/0003* (2013.01); *A63B 60/46* (2015.10); *A63B 69/3667* (2013.01); *A63B 71/0622* (2013.01); *A63B 2024/0034* (2013.01); *A63B 2102/32* (2015.10); *A63B 2220/30* (2013.01); *A63B 2220/35* (2013.01); *A63B 2220/40* (2013.01); *A63B 2220/52* (2013.01); *A63B 2220/806* (2013.01); *A63B 2220/833* (2013.01); *A63B 2225/54* (2013.01)

(58) Field of Classification Search
CPC . A63B 71/0622; A63B 24/0003; A63B 60/46; A63B 69/3658; A63B 69/3667
See application file for complete search history.

(56) References Cited

U.S. PATENT DOCUMENTS

| | | | | |
|---|---|---|---|---|
| 4,070,018 A | * | 1/1978 | Hodges | A63B 63/00 473/192 |
| 5,221,082 A | * | 6/1993 | Curshod | A63B 24/0021 434/252 |
| 5,826,578 A | * | 10/1998 | Curchod | A61B 5/1121 600/595 |
| 2004/0127302 A1 | * | 7/2004 | Jones | A63B 57/0006 473/134 |
| 2004/0198524 A1 | * | 10/2004 | Kwon | A63B 24/0021 473/151 |

(Continued)

*Primary Examiner* — Steve Rowland
(74) *Attorney, Agent, or Firm* — Rogers Towers, P.A.; Joseph P. Kincart

(57) ABSTRACT

An apparatus and method for repetitively training a golf swing is disclosed. In some embodiments of the present apparatus, foot placement guides are provided to align a golfer's stance relative to a golf ball on a tee. Motion and other data capture create a swing profile for the golfer's swing, which is compared to the swing of a golf Pro, thus giving swing feedback to the golfer. The apparatus automatically resets the ball position after the swing, allowing the golfer to repeat the swing based on the received feedback while isolating other variables (such as inaccurate resetting of foot position).

16 Claims, 4 Drawing Sheets

(56) References Cited

U.S. PATENT DOCUMENTS

| | | | |
|---|---|---|---|
| 2007/0196800 A1* | 8/2007 | Douthit | A63B 24/0003 434/252 |
| 2007/0238539 A1* | 10/2007 | Dawe | A63B 24/0003 473/131 |
| 2008/0200287 A1* | 8/2008 | Marty | A63B 24/0003 473/459 |
| 2009/0029754 A1* | 1/2009 | Slocum | A63B 24/0087 463/5 |
| 2010/0184496 A1* | 7/2010 | Nicora | A63B 69/36 463/5 |
| 2011/0273562 A1* | 11/2011 | Dawe | A63B 24/0021 348/139 |

* cited by examiner

APPARATUS AND METHOD FOR REPETITIVE TRAINING OF GOLF SWING

CROSS REFERENCE TO RELATED APPLICATIONS

The present application claims priority to Provisional Patent Application Ser. No. 62/569,890, filed Oct. 9, 2017, and entitled APPARATUS AND METHOD TO TRAIN FOR REPETITIVE GOLF SWING.

FIELD OF THE DISCLOSURE

The present disclosure relates to an apparatus and method for providing repetitive training of a golf swing.

BACKGROUND OF THE DISCLOSURE

People of all ages love golf, both as a competitive sport and as recreation. Regardless of a player's motivation to play golf, the player will usually wish to improve the player's skill at the game. This requires proper training, which can come in generally three nonexclusive forms: (1) instruction in the proper mechanics of movement (e.g., an ideal golf swing); (2) feedback to identify differences between the ideal mechanics and the actual mechanics by the athlete; and (3) repetition of skills, either to reinforce the "muscle memory" of the athlete with respect to ideal mechanics, and/or to increase endurance.

Golf may be taken up by players at substantially any age, at least at a nonprofessional skill level of play, and does not necessarily require extensive training if the player is more interested in recreation than competition. However, there exists a risk that a player who takes up a sport without sufficient training may acquire muscle memories of non-ideal mechanics. Such muscle memories may be difficult to unlearn.

It is undesirable to attain muscle memories of bad mechanics because golf depends heavily upon the mechanics of certain movements, such as an initial drive of a golf ball from a tee. Compared to a poorly driven golf ball, a well driven golf ball struck using ideal mechanics may travel many tens of yards farther, or travel a straighter path, or have a preferred amount of spin to control "bite". Yet, golf players who take up the sport and want to play at a competitive level often do not have access to adequate training facilities to learn and incorporate the ideal mechanics.

Therefore, what is needed is an improved method and apparatus for golf training that addresses the shortcomings identified above.

SUMMARY OF THE DISCLOSURE

Embodiments in accordance with the present disclosure include methods and apparatus to provide training of a repetitive sporting motion, based upon an instructor example.

One general aspect includes a system to provide training for a repetitive sporting motion, including: a first subsystem, which includes a display positioned to receive impact from a first ball that has been launched from a ball positioning apparatus, and which display also shows an image visible to a first person. The image may relate to the instructor example. The first subsystem also includes a motion capture apparatus to capture multiple sequential sporting motions by the first person, as well as a motion detector to track a first body motion of the first person during a first sporting motion interacting with the first ball at a set position. Additionally, the first subsystem includes a processor coupled to a database, the processor programmed to save a captured motion path based upon the first body motion, an identification of the image and an identification of the first body motion. Importantly, the first subsystem also includes a ball reset apparatus to present the first ball in the set position and to provide a second ball in the set position based upon removal of the first ball from the set position and impacting the display resulting from the first body motion. The first subsystem also includes the processor is additionally operative to receive from the motion detector a tracking of a second body motion interacting with the second ball at the set position. Other embodiments of this aspect include corresponding computer systems, apparatus, and computer programs recorded on one or more computer storage devices, each configured to perform the actions of the methods.

Implementations may include one or more of the following features. The system may additionally include a communication link to a second subsystem, in which the second subsystem includes: a display to show the image to a second person; a motion display to show a motion to the second person; a motion capture apparatus to capture a sporting motion by the second person, responsive to an image; and a comparison apparatus to compare the sporting motion by the first person with the sporting motion by the second person. The system may additionally include one or more swing guide discs placed proximate to the first person. The system additionally includes a foot placement guide. In an additional embodiment, the foot placement guide includes a mat, a first and a second string removably attached to the mat, and where the first string is placed at approximately a ninety degree angle with respect to the second string. The foot placement guide may further include one or more beads fixedly attached to one or more of: the first string and the second string, where the one or more beads measure between approximately $\frac{1}{16}$" and $\frac{1}{8}$" in diameter. A first foot and a second foot of the first person may be aligned with the first string and the second string. The foot placement guide may also include pressure sensors. The ball reset apparatus may also include a golf tee, a plurality of golf balls, and a ball reservoir. One or more of the plurality of golf balls may include an embedded rf communication transmitter. The system may additionally further include a golf club, which golf club includes an embedded rf communication transmitter. Implementations of the described techniques may include hardware, a method or process, or computer software on a computer-accessible medium.

One general aspect includes a method for repetitive training of a golf swing, the method including: a) placing two feet of a first golfer in a first set of respective positions for a first golf swing by the first golfer with a first golf club; b) automatically setting a first golf ball on a golf tee device in a position within a distance suitable for striking the golf ball with the first golf club while the two feet of the first golfer remain in the first set of respective positions; c) tracking movement of the first golfer through a first golfer swing of the golf club causing the golf club to impact the first golf ball; d) tracking flight of the first golf ball resulting from the golf club impacting the first golf ball during the first golf swing; storing a representation of the flight of the first golf ball in a system capable of generating a multimedia representation of the flight of the first golf ball; f) while the two feet of the first golfer remain in the first set of respective positions, automatically placing a second golf ball on the golf tee; and g) repeating steps b) through e) for the second golf ball while the two feet of the first golfer continue to remain in the first set of respective positions. Other embodiments of this aspect include corresponding computer systems, apparatus, and computer programs recorded on one or more computer storage devices, each configured to perform the actions of the methods.

In some implementations, the method may additionally include the step of comparing the tracked movement of the first golfer to a desired golf swing form via the steps of: (1) using a motion detector apparatus to track a motion of a second golfer performing a second golf swing including the desired golf swing form and (2) comparing an arc of movement of the first golfer through the first golf swing and an arc of movement of the second golfer. This implementation may further include the step of displaying on a screen a projected trajectory of the first golf ball after the first golfer swing. This implementation may further include the step of displaying on a screen deviations in movement patterns between the first golfer and the second golfer. The method may further include placing one or more guide discs proximate to the first golfer. In such implementations, a position of at least one of the guide discs relative to the first golfer may be approximately the same as the position of the end of the second golfer's backswing. Similarly, in other implementations, a position of at least one of the guide discs relative to the first golfer may be approximately the same as the position of the end of the second golfer's follow through. In other implementations, the angular orientation of at least one of the guide discs relative to a face of a golf club held by the first golfer may be approximately the same as the angular orientation of a face of a golf club held by the second golfer. Even without guide discs, the step of replacing a second golf ball on the golf tee may be performed using a ball reset apparatus. In such implementations, the ball reset apparatus may include the golf tee, a plurality of golf balls, and a ball reservoir. Implementations of the described techniques may include hardware, a method or process, or computer software on a computer-accessible medium.

BRIEF DESCRIPTION OF THE DRAWINGS

The accompanying drawings, that are incorporated in and constitute a part of this specification, illustrate several embodiments of the disclosure and, together with the description, serve to explain the principles of the disclosure.

The drawings are not necessarily drawn to scale unless clearly indicated otherwise.

DETAILED DESCRIPTION

In the following sections, detailed descriptions of examples and methods of the disclosure will be given. The description of both preferred and alternative examples though thorough are exemplary only, and it is understood that to those skilled in the art that variations, modifications, and alterations may be apparent. It is therefore to be understood that the examples do not limit the broadness of the aspects of the underlying disclosure as defined by the claims.

Figure 1:
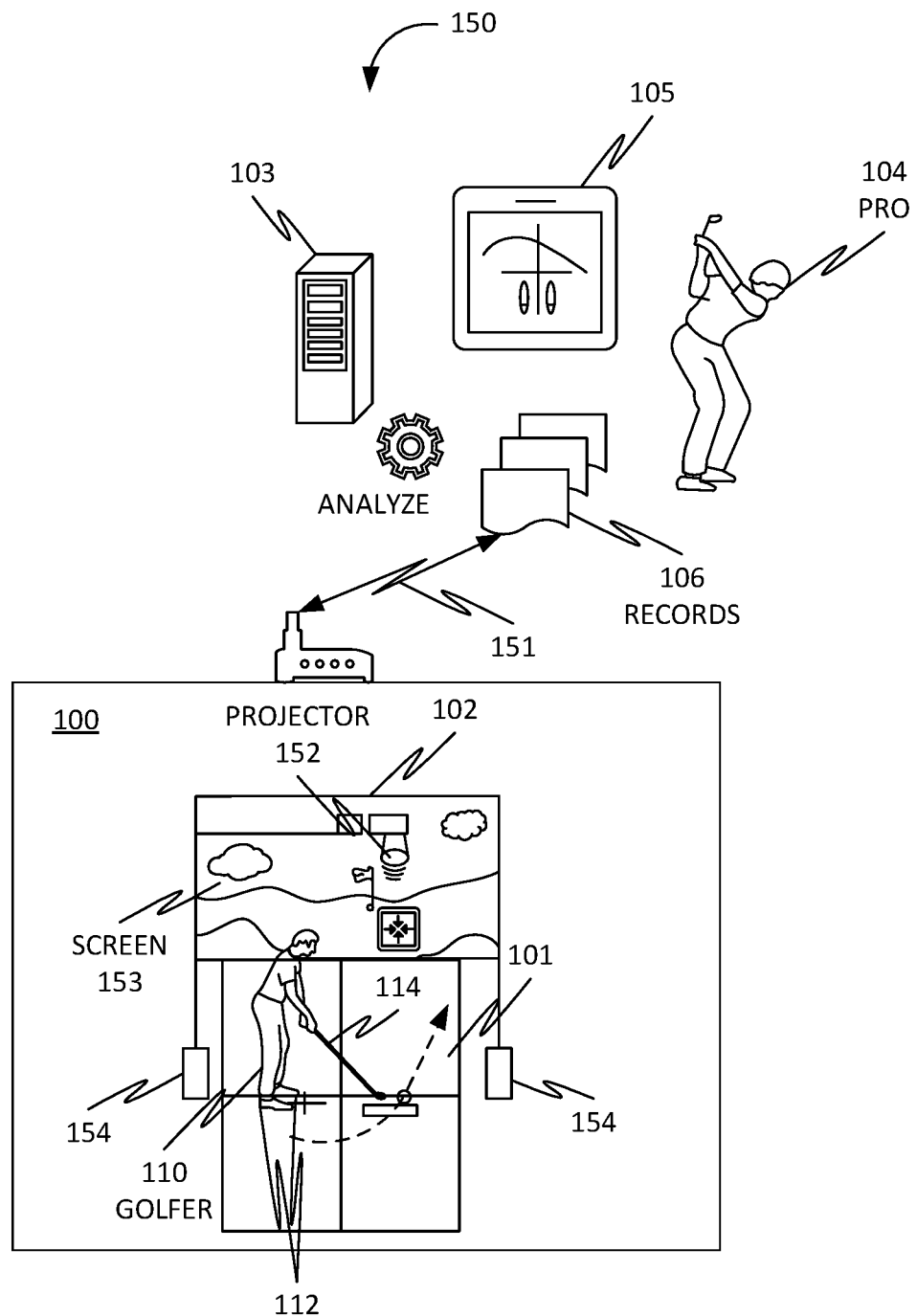
FIG. 1 illustrates a system in accordance with the present disclosure.

FIG. 1 illustrates system 150 to train an athlete to repetitively perform a sporting motion (e.g., a golf swing) in accordance with an embodiment of the present invention. System 150 illustrates an instructor such as professional player ("Pro") 104 creating a motion capture of a physical activity such as a golf swing, to be viewed or replayed either in real time or later from a recording by a student player such as golfer 110. The motion capture may involve apparatus such as a video recorder or infrared sensor, optionally combined with a motion capture suit and associated analytics (e.g., to create a vector model or 3-D model of Pro 104). Although system 150 will be described with reference to training for a golf swing, system 150 is adaptable to train for other kinds of sporting motions such as a tennis serve, a baseball swing, etc.

System 150 is usable to train golfer 110 to maintain proper posture while practicing multiple golf swings. In particular, system 150 trains golfer 110 to maintain their body in a specific quantifiable position with little or no movement of certain body parts (e.g., no movement of feet) while swinging a golf club 114. In some embodiments, system 150 accomplishes this through foot position markers 112. In some embodiments, foot markers 112 are placed in the correct stance for the desired golf swing. In other embodiments, foot position markers 112 comprise a means for detecting pressure profiles, such as scales or pressure sensors, to monitor the golfer's 110 weight distribution. In some embodiments, system 150 can notify golfer 110 of incorrect body movement or weight distribution through audio notifications, such as an alarm, or visual notifications, such as a display on screen 153 indicating the difference between ideal body positioning and the golfer's 110 actual body positioning. By ensuring that golfer 110 has good body positioning on each swing, embodiments thus use repetition to develop "muscle memory" in golfer 110.

System 150 is spread across two locations or subsystems. In some embodiments, an instructional swing may be recorded at a first location by a Pro 104, along with a computer-based recording and analysis system 103, and a display screen 105. Display screen 105 may be used to show a golfer's eye view of a golf course, i.e., a contextual view of a golf course as seen by a golfer, such as at a tee or other spot such as a fairway or a sand trap. Pro 104 demonstrates a motion of a suitable instructional swing and hits a golf ball as if Pro 104 were physically at a golf course shown on display screen 105. Contemporaneously, recording and analysis system 103 records the movements (or lack thereof) by Pro 104 as the golf ball is struck. The recorded movements may include a swing pattern (e.g., a profile versus time of a position of the golf club or of certain body parts (e.g., hands, feet, shoulders, etc.)) of Pro 104. A net, screen or other ball catching device may be used to capture the struck golf ball before the ball can strike an object or person and do any damage. The images captured by recording and analysis system 103, and a record of golf course images shown when a golf ball was struck, may be stored in a records database 106 as instructional examples of a repetitive sporting motion. A primary communication interface (e.g., a USB link or Ethernet link) may link the recording and analysis system 103 to records database 106.

Records database 106 may be accessible from a remote location by use of a secondary communication interface 151, such as an Ethernet interface or a wireless interface. Specifically, records database 106 may be accessible via communicative interface 151 from a second location 100 that forms a portion of system 150.

Second location 100 or subsystem is where golfer 110 can practice the repetitive sporting motion, based upon instructional examples provided by Pro 104. For example, second location 100 may include a video subsystem 102 to display on a screen various contextual views of a golf course, the context being relevant to instructional examples of the repetitive sporting motion. Optionally, video display subsystem 102 also may include a second motion capture apparatus (similar to the first motion capture apparatus, used in connection with Pro 104) to record golfer 110's multiple sequential sporting motions as golfer 110 attempts to perform the same repetitive sporting motion as that had been recorded by Pro 104. Video display subsystem 102 may include a projector 152, a screen 153, and one or more optional cameras 154. The screen 153 may be positioned to receive impact from golfer 110's golf ball.

Second location 100 also may include a foot placement guide 101 to show proper posture, i.e., where golfer 110 should place his/her feet when performing the repetitive sporting motion. For example, the foot placement guide may include a mark placed on the floor, or visible on the floor, such as an outline of each foot, or an "X" for each foot, and so forth.

In some embodiments, foot placement guide 101 may include markings on the turf-like covering that are usable by golfer 110 to gauge his/her alignment compared to an ideal alignment. The alignment may be useful for aligning the feet of golfer 110 and/or a golf club 114 held by golfer 110. When aligning a golf club 114, the alignment may be indicated by matching lines on the golf club 114 to lines on turf during a swing, or by wear mark on the golf club 114.

In some embodiments, video display subsystem 102 may be used to record foot alignment of golfer 110. The foot alignment may be captured by, e.g., a camera image which may further include coordinates (e.g., an (X, Y) graticule), or by pressure sensors. Pressure sensors may capture the left and right feet separately, and may capture different portions of each foot separately (e.g., heel pressure and toe pressure). The pressure measurements may be captured as a profile during a golf swing, such that a graph of pressure during the golf swing may be produced. For example, if a swing takes 0.1 seconds, and at least 5 pressure measurements during the swing are desired, then the pressure measurements should be made at a rate of at least 50 measurements per second per sensor.

Embodiments in accordance with the present disclosure may include an ability to track separate users, e.g., in a multi-user environment, so that performance and progress of multiple golfers may be tracked over time.

In some embodiments, system 150 may relate the measured movement of golfer 110 to a physics model in order to provide feedback to golfer 110 about suggested changes (e.g., to a stance, to a club grip, etc.) in order to achieve an optimal golf swing.

In some embodiments, system 150 may be tuned to provide advice or instructions for a specific golf course and/or for a specific hole at a golf course. Such instructions may be useful for, e.g., training for an important golf tournament (e.g., the Masters Golf Tournament), in order to provide an optimal swing for golfer 110, for the specific golf course and/or for a specific hole.

In some embodiments, system 150 may be programmed to simulate various wind and/or moisture conditions. For example, wind may be modeled as blowing from a configurable direction and configurable mean speed. Wind gusts may be modeled further by including a variable component to the wind, e.g., a variable change in speed lasting several seconds at a time. Moisture conditions may be modeled by, e.g., how a golf ball bounces, rolls, and/or "bites" on a green or fairway.

As noted earlier, embodiments help promote development of "muscle memory" in golfer 110 in order to improve the mechanics of a repetitive sporting motion. Repeatability without changing body stance helps build the muscle memory. It is expected that typically hundreds of swings in a relatively short amount of time (e.g., within 1 hour in one session) would be effective.

Some embodiments may store settings and progress by golfer 110 on a per-golfer basis, in order to allow golfer 110 to resume training at a later time or date, at or near a point at which golfer 110 had stopped training. For example, embodiments may allow golfer 110 to swing 100 times per day for several days in a row on a particular hole at a particular course.

Some embodiments may allow golfer 110 to store a best swing at each hole for a particular course. In another aspect, some implementations may include accelerometers, sensors, transmitters, transducers or other device that enables details of a swing motion to be registered by an automated apparatus and track the arc of the swing. For example, one or more such devices may be attached to one or both of a golfer's arms, torso or other body part and a relative movement may be recorded.

Some embodiments may allow a server to track and save the actions of Pro 104 or golfer 110 for later analysis. Server functions may be embedded in recording and analysis system 103, or a separate server may be located at second location 100, depending upon what actions, measurements, and/or parameters are being stored. Some embodiments may include sensors embedded into a golf club and/or a golf ball, to measure parameters such as swing velocity, acceleration, swing angles, ball trajectory, ball spin, and so forth. The golf club and/or golf ball may include an embedded RF communication capability (e.g., near field communications, Bluetooth™, etc.) in order to transmit the parameters measured by the golf club and/or golf ball. The parameters may include an identification of the equipment (e.g., manufacturer and model number of the golf ball and/or golf club), to be saved along with the record of performance saved by system 150. Other parameters, conditions, or measurements that may be saved may include tee type, tee height, swing specifics (e.g., arc path or swing, back swing line to backswing point, end point (i.e., follow though swing)), position of eyes of golfer 110, velocity of certain parts of the golf club (e.g., at the head) when the golf ball is struck, as well as during other points within the golf swing such as before the ball is struck and during the follow-through, angle of club in relation to feet and/or ball and/or desired destination point, and so forth.

In some embodiments, the saved actions, measurements, and/or parameters data may be analyzed using "big data" and/or artificial intelligence (AI) techniques. For example, AI techniques may involve unstructured query of variables and results. These analytics may be displayed on screen 153 in some embodiments.

Figure 2:
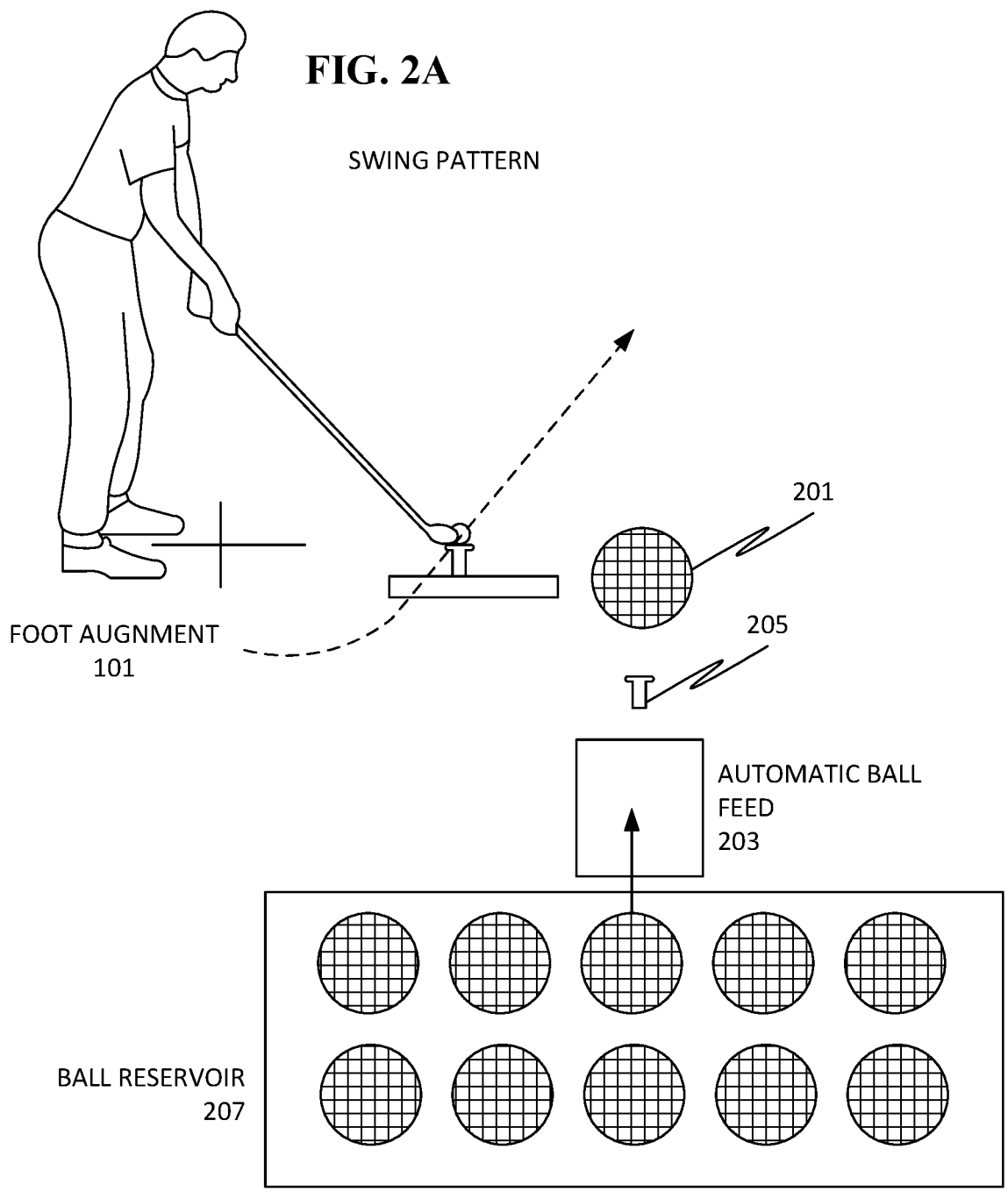
FIG. 2 illustrate portion of the system during usage, in accordance with the present disclosure.

FIG. 2 illustrates a more detailed view of golfer 110 preparing to strike golf ball 201, with the help of foot placement guide 101 and the posture it indicates. FIG. 2 further illustrates usage of an automated golf ball feed and placement apparatus 203, which is used to place golf ball 201 in position for being struck by golfer 110 during practice, e.g., by placing golf ball 201 upon a tee 205. Golf ball feed and placement apparatus 203 includes a reservoir 207, which stores additional golf balls 201 until they are needed by golfer 110.

Tee 205 may have approximately the same dimensions as a traditional wood or plastic tee. However, unlike a traditional tee, tee 205 may be a flexible golf ball holder fixedly attached to a base and coupled to a sensor. The sensor may sense when a golf ball 201 has been struck (e.g., by detection of motion by tee 205, or change in weight upon tee 205). In usage, when golfer 110 strikes one golf ball 201, the fixedly attachment of tee 205 to a base facilitates keeping tee 205 in place for a next swing. The sensor may trigger golf ball feed and placement apparatus 203 to retrieve another golf ball from reservoir 207, and place the retrieved golf ball 201 onto tee 205. Golf ball feed and placement apparatus 203 is useful to reduce the time needed to put another golf ball 201 in position to be struck by golfer 110, so that more repetitions of the repetitive sporting motion may be practiced by golfer 110 within a given amount of time. Additionally, in some embodiments, the tee 205 may have an adjustable height relative to the ground.

Figure 3:
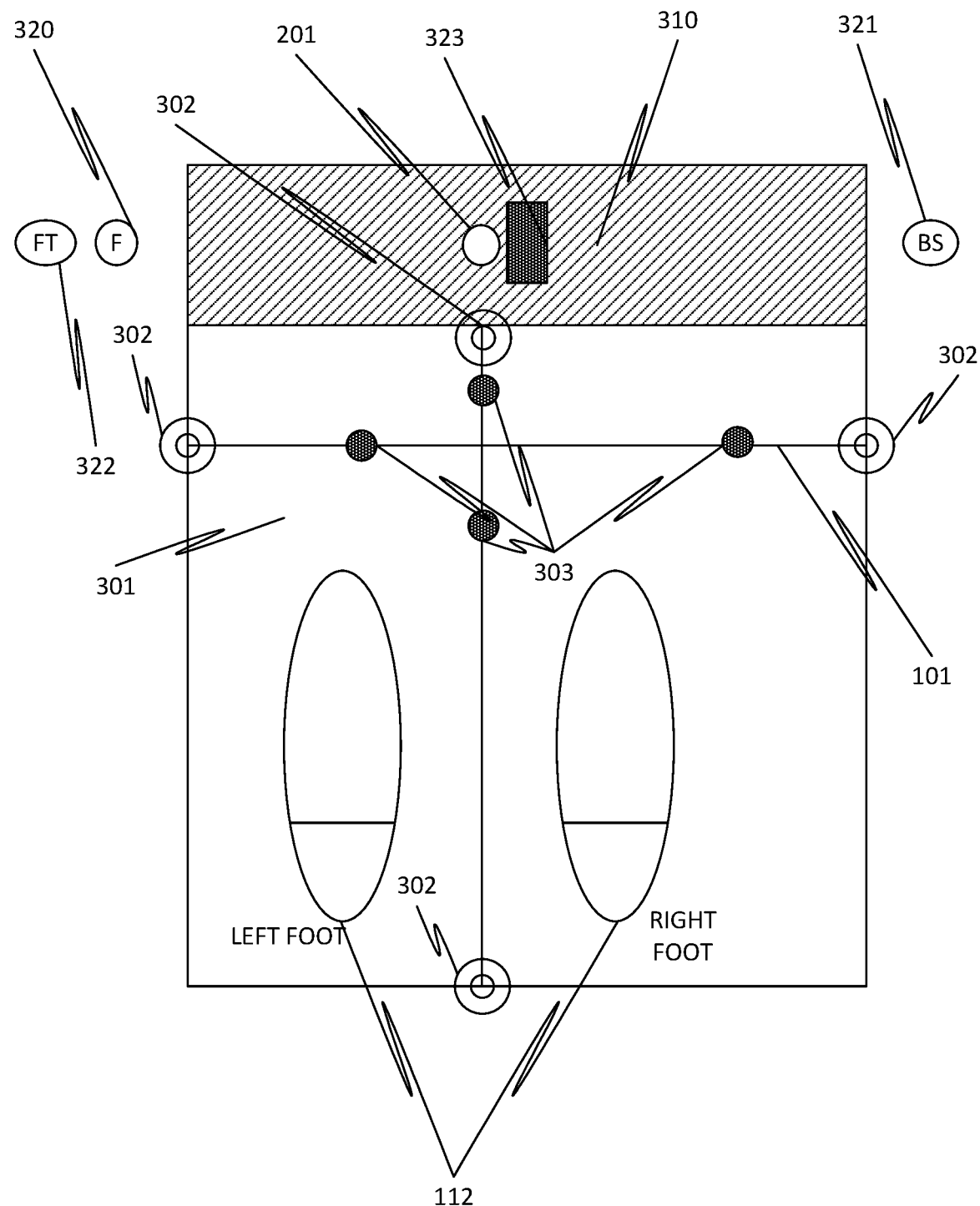
FIG. 3 illustrates an exemplary user guide, in accordance with an embodiment of the present invention.

FIG. 3 illustrates a foot placement guide 101 in greater detail. In some embodiments, foot placement guide 101 rests on a standing mat 301. The standing mat 301 may comprise a material designed to be comfortable to stand on, such as rubber, carpeting materials, vinyl, or wood, or else may comprise a material designed to simulate a golfing environment, such as natural or artificial grass, turf, or sand. Foot placement guide 101 may include an indication of posture, i.e., where and with what orientation (e.g., direction the toes are pointed, amount of splay, etc.) golfer 110 should place his/her feet. The indication may be made from physical objects placed on a floor, e.g., adjustable string with removable attachment devices, pins in holes, tacks in substrate, a hook-and-loop fastener such as Velcro®, beads 303 used as a offset to hold the string above turf (1/16 inch to 1/8 diameter with hole in middle), and so forth. In an exemplary embodiment, foot placement guide 101 may be secured to the standing mat 301 by strings with clips 302 on the ends of the strings, and beads 303 to provide setoff between the strings and the standing mat 301. This is highly desirable because existing implementations of foot placement guides are easily disturbed if, for example, golfer 110 accidentally hits the string with their foot or the club. The combination of clips 302 and beads 303 can prevent such a disruption. In other embodiments, foot placement guide 101 may be formed from a light or image projected onto the floor. For example, the light or image may be spot lights, LEDs light, laser light, an image or shadow of an image made from a lens cover, and so forth.

Golf ball 201 sits on a striking surface 310 adjacent to the standing mat 301. The striking surface 310 may include a turf-like covering to simulate a golf course (e.g., a teeing ground, a fairway, a putting green, etc.). In some embodiments, a surface simulating a sand trap may be provided.

In exemplary embodiments, the foot placement guide 101 may additionally comprise one or more guide discs 320-322. As shown in FIG. 3, one of the guide discs, face disc 320, may correspond to a desired orientation of the face 323 of the chosen golf club. In some embodiments, a backswing disc 321 corresponds to a desired orientation and distance of the golfer 110's backswing. Those skilled in the art will understand that amateur golfers frequently utilize shallow swings, and backswing disc 321 assists in fixing this problem. In some embodiments, a follow through disc 322 is provided, corresponding to the direction and magnitude of the follow through of the golf swing. This is particularly useful when setting up a desired fade or cut. For example, a golfer on a golf course seeking to hit a fade shot might pick a target a few feet ahead of the tee (e.g., a leaf) that is in line with the left edge of the fairway. The golfer may treat that target as the center stripe for the swing, but change the direction of the face of the club slightly to the right. The present disclosure accommodates this practice by equating the target to the follow through disc 322. Changing the orientation of these guide discs 320-322 relative to each other and relative to the golfer 110's stance may assist in perfecting the golf swing. For example, a golfer seeking to drive a ball straight may orient the discs differently than a golfer who is chipping the ball or desiring to hit the ball with a draw. The guide discs 320-322 also assist in remote instruction of golfer 110. For example, suppose golfer 110 wants to learn how to hit Famous Golfer's Fade Shot. An instructor (e.g., the Pro 104) can remotely—either live or by pre-recorded video—instruct the golfer 110 on the appropriate placement of the guide discs 320-322, according to how Famous Golfer orients her swing and stance when setting up her Fade Shot.

In some embodiments, one or more of the guide discs 320-322 may be replaced by other visual aids. By way of nonlimiting example, this may include a laser pointed to the golf ball 201 to indicate the correct point on which to strike the golf ball 201.

Embodiments in accordance with the present disclosure are usable for rapid prototyping, in order to quickly evaluate the performance of certain equipment (e.g., golf balls, golf clubs, custom clubs used by a golfer), incorporate improvements based upon the evaluation, and retest using the improved equipment. Rapid prototyping may work better when the equipment is being used and tested by a skilled golfer (e.g., pro golfer 104) so that changes in measured performance is more likely to be due to changes in equipment design rather than variations in performance by the golfer. Alternatively, in some embodiments, golfer performance may be normalized or calibrated by usage of measured golfer performance (e.g., estimated distance traveled by a struck golf ball may be normalized or calibrated by the measured club head speed).

Figure 4:
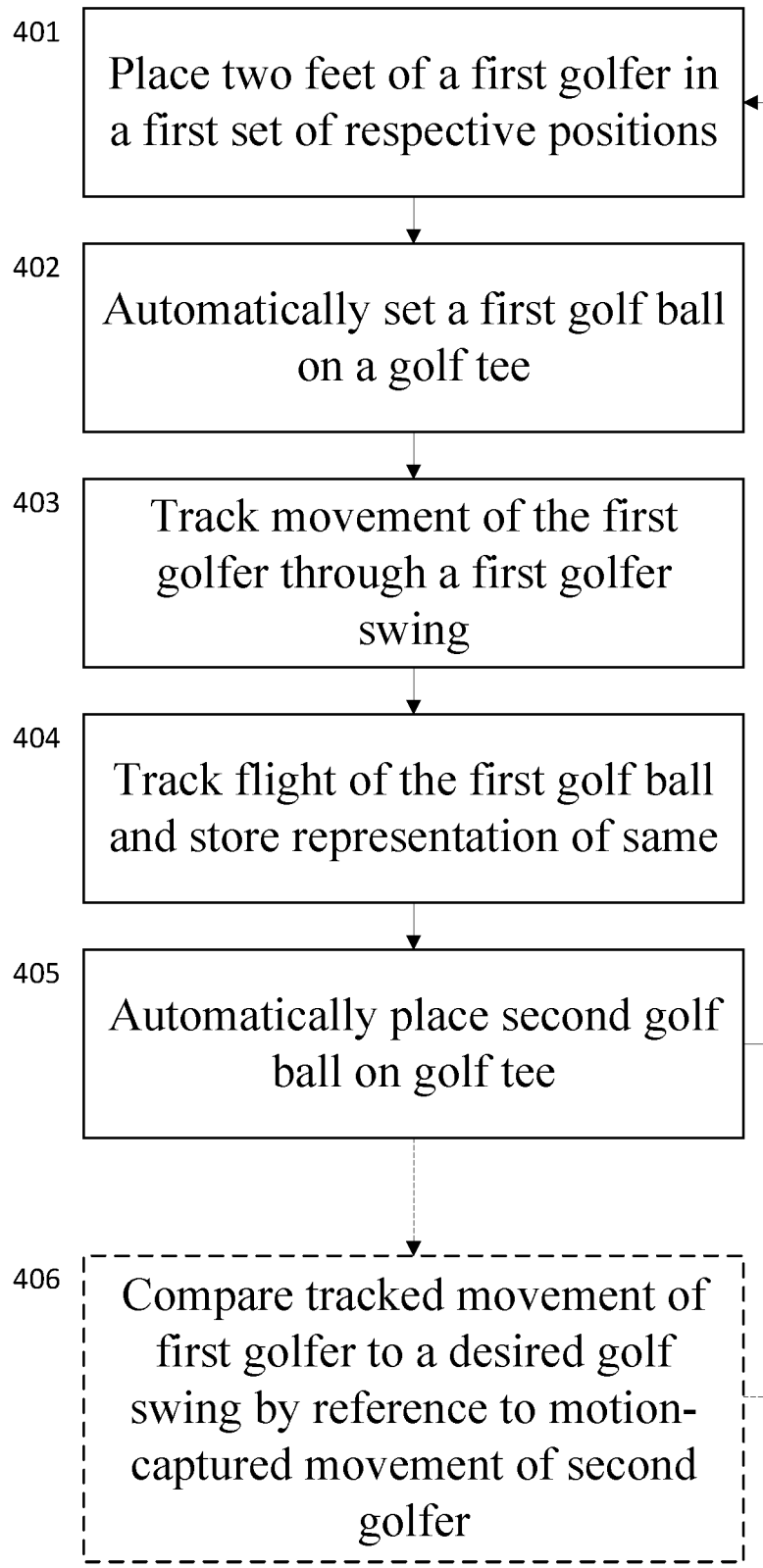
FIG. 4 illustrates an exemplary embodiment of a method for repetitively training a golf stroke.

FIG. 4 illustrates an exemplary method 400 for repetitively training a golf swing. At step 401, two feet of a first golfer are placed in a first set of respective positions. By way of nonlimiting examples, the respective positions may be determined by reference to structures like the foot placement guide 101, or by projected light. The respective positions may also be on top of pressure-sensitive panels, which in some embodiments can notify the first golfer of incorrect weight distribution of the first golfer's feet. Such notifications may include colored lights on the panels.

At step 402, a first golf ball is automatically set on a golf tee. By way of nonlimiting example, this may be accomplished using a specialized ball reset apparatus. In some embodiments, the ball reset apparatus comprises the tee and one or more golf balls stored approximately adjacent to the tee. In an exemplary embodiment, the one or more golf balls are stored in a reservoir underneath and next to the tee. An ordinary tee is a small peg with a top circular portion and a bottom spike portion. The tee is used by driving the spiked portion into the ground and placing a golf ball on the top circular portion. The tee contemplated in this exemplary embodiment instead comprises a cylindrical portion of approximately uniform thickness that is installed underground and raised above the ground through a hole in the ground. In this exemplary embodiment, the ball reservoir is connected to this hole. In this embodiment, at steps 402 and

405, the tee retracts into the hole, allowing a ball to move from the ball reservoir to the top of the tee. The tee then rises back above ground with a ball mounted on top, ready to be struck by the first golfer.

At step 403, the golfer 110 takes a golf swing, and the golfer 110's movement is tracked through the swing. By way of nonlimiting example, this may be accomplished by a video recorder or infrared sensor, optionally combined with a motion capture suit and associated analytics (e.g., to create a vector model or 3-D model of Pro 104). In some embodiments, undesirable deviations from the desired swing profile determined in step 401 may trigger warnings to the golfer 110. These warnings may include, without limitation, audio cues such as a loud buzzer, visual cues displayed on a display screen (e.g., screen 153), or visual cues displayed on the golf ball 201.

At step 404, the flight of the first golf ball is tracked. This may be accomplished by a video recorder, infrared sensor, or RF or other EMF transmitters in the golf ball. In these embodiments, a computer in logical connection with the appropriate receiver receives the signal from the golf ball and has software operative to store the location and/or trajectory of the golf ball. Accordingly, a representation of the flight of the first golf ball is stored and tracked. In some embodiments, this representation is displayed on a screen proximate to the golfer.

At step 405, a second golf ball is automatically placed on the golf tee. In some embodiments, this is accomplished using the same automated means as used at step 402. Accordingly, at the conclusion of step 404, the golfer 110 is in the same position as they were in at the start of step 402, prior to swinging the golf club. This allows the golfer 110 to make adjustments based on the feedback and flight display provided in step 404 and take another golf swing, while isolating all other variables that may impact the swing, such as weight distribution and foot placement. Steps 402-405 may then be repeated as many times as necessary. It is important to emphasize that the speed of repetition enabled by method 400, combined with its feedback systems and ability to isolate the mechanics that need to be trained, allow for optimal training of muscle memory in golfer 110.

Optionally, at step 406, the tracked movement of the first golfer may be compared to the tracked movement of a second golfer. The second golfer may be an instructor, such as Pro 104. In some embodiments, the swing of the second golfer is determined by one or more of: motion capture, accelerometer in the second golfer's golf club, accelerometer in the golf ball, geolocation sensors in the golf ball or golf club, Bluetooth, IR, other sensors, or the detection means used in step 403. In some embodiments, this swing profile is stored in analysis system 103. In some embodiments, the swing profile is further determined with reference to one or more guide discs, such as discs indicating an appropriate direction and magnitude of the backswing and/or the follow through. In some embodiments, a display connected to the analysis system or computer and proximate to the first golfer may show the first golfer the movement of the second golfer. In some embodiments, the display may also show the first golfer deviations between the movement of the first golfer and the movement of the second golfer.

A number of embodiments of the present disclosure have been described. While this specification contains many specific implementation details, there should not be construed as limitations on the scope of any disclosures or of what may be claimed, but rather as descriptions of features specific to particular embodiments of the present disclosure. While embodiments of the present disclosure are described herein by way of example using several illustrative drawings, those skilled in the art will recognize the present disclosure is not limited to the embodiments or drawings described. It should be understood the drawings and the detailed description thereto are not intended to limit the present disclosure to the form disclosed, but to the contrary, the present disclosure is to cover all modification, equivalents and alternatives falling within the spirit and scope of embodiments of the present disclosure as defined by the appended claims.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted the terms "comprising", "including", and "having" can be used interchangeably.

Certain features that are described in this specification in the context of separate embodiments can also be implemented in combination in a single embodiment. Conversely, various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while method steps may be depicted in the drawings in a particular order, this should not be understood as requiring that such operations be performed in the particular order shown or in a sequential order, or that all illustrated operations be performed, to achieve desirable results.

Certain features that are described in this specification in the context of separate embodiments can also be implemented in combination in a single embodiment. Conversely, various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order show, or sequential order, to achieve desirable results. In certain implementations, multitasking and parallel processing may be advantageous. Nevertheless, it will be understood that various modifications may be made without departing from the spirit and scope of the claimed disclosure.

In certain implementations, multitasking and parallel processing may be advantageous. Nevertheless, it will be understood that various modifications may be made without departing from the spirit and scope of the claimed disclosure.

I claim:

1. A system to provide training for a repetitive sporting motion, comprising:
   a first subsystem, comprising:
     a display positioned to receive impact from a first ball that has been launched from ball positioning apparatus and to show an image visible to a first person;
     a motion capture apparatus to capture multiple sequential sporting motions by the first person;
     a motion detector to track a first body motion of the first person during a first sporting motion interacting with the first ball at a set position;
     a processor coupled to a database, the processor programmed to save a captured motion path based upon the first body motion, an identification of the image and an identification of the first body motion;
     a ball reset apparatus to present the first ball in the set position and provide a second ball in the set position based upon removal of the first ball from the set position and impacting the display resulting from the first body motion;
     the processor is additionally operative to receive from the motion detector a tracking of a second body motion interacting with the second ball at the set position;
     a communications device;
   a second subsystem with a communication link to the first subsystem, the second subsystem comprising:
     a display to show the image to a second person;
     a motion display to show a motion to the second person;
     a motion capture apparatus to capture a sporting motion by the second person, responsible to an image;
     a comparison apparatus to capture the sporting motion by the first person with the sporting motion by the second person; and
   a foot placement guide comprising a mat, a first and a second string removably attached to the mat, wherein the first string is placed at approximately a ninety degree angle with respect to the second string.

2. The system of claim 1, additionally comprising one or more swing guide discs placed proximate to the first person.

3. The system of claim 1, wherein the foot placement guide further comprises one1 or more beads fixedly attached to one or more of: the first string and the second string, wherein the one or more beads measure between approximately 1/16" and 1/8" in diameter.

4. The system of claim 1, wherein the foot placement guide comprises pressure sensors.

5. The system of claim 2, further comprising a golf club, which golf club comprises an embedded RF communication transmitter.

6. A method for repetitive training of a golf swing, the method comprising:
   a) placing two feet of a first golfer in a first set of respective positions for a first golf swing by the first golfer with a first golf club;
   b) placing one or more guide discs proximate to the first golfer;
   c) automatically setting a first golf ball on a golf tee device in a position within a distance suitable for striking the golf ball with the first golf club while the two feet of the first golfer remain in the first set of respective positions; c) tracking movement of the first golfer through a first golfer swing of the golf club causing the golf club to impact the first golf ball;
   d) tracking flight of the first golf ball resulting from the golf club impacting the first golf ball during the first golf swing;
   e) storing a representation of the flight of the first golf ball in a system capable of generating a multimedia representation of the flight of the first golf ball;
   f) while the two feet of the first golfer remain in the first set of respective positions, automatically placing a second golf ball on the golf tee;
   h) repeating steps c) through f) for the second golf ball while the two feet of the first golfer continue to remain in the first set of respective positions; and
   i) comparing the tracked movement of the first golfer to a desired golf swing form via the steps of: using a motion detector apparatus to track a motion of a second golfer performing a second golf swing comprising the desired golf swing form; and comparing an arc of movement of the first golfer through the first golf swing and an arc of movement of the second golfer.

7. The method of claim 6, further comprising the step of displaying on a screen a projected trajectory of the first golf ball after the first golfer swing.

8. The method of claim 7, further comprising the step of displaying on a screen deviations in movement patterns between the first golfer and the second golfer.

9. The method of claim 6, wherein the step of replacing a second golf ball on the golf tee is performed using a ball reset apparatus.

10. The method of claim 9, wherein the ball reset apparatus comprises the golf tee, a plurality of golf balls, and a ball reservoir.

11. The method of claim 6, wherein a position of at least one of the guide discs relative to the first golfer is approximately the same as the position of the end of the second golfer's backswing.

12. The method of claim 6, wherein a position of at least one of the guide discs relative to the first golfer is approximately the same as the position of the end of the second golfer's follow through.

13. The method of claim 6, wherein the angular orientation of at least one of the guide discs relative to a face of a golf club held by the first golfer is approximately the same as the angular orientation of a face of a golf club held by the second golfer.

14. A system to provide training for a repetitive sporting motion, comprising:

a radio frequency (RF) communication transmitter embedded in at least one of: a first golf ball and a golf club;
a first subsystem, comprising:
   a display positioned to receive impact from the first ball that has been launched from ball positioning apparatus via contact with the golf club and to show an image visible to a first person;
   a motion capture apparatus to capture multiple sequential sporting motions by the first person;
   a motion detector to track a first body motion of the first person during a first sporting motion interacting with the first ball at a set position;
   a processor coupled to a database, the processor programmed to save a captured motion path based upon the first body motion, an identification of the image and an identification of the first body motion;
   a ball reset apparatus comprising a golf tee, a plurality of golf balls, and a golf reservoir, wherein the ball reset apparatus is operable to present the first ball in the set position and provide a second ball in the set position based upon removal of the first ball from the set position and impacting the display resulting from the first body motion;
   the processor is additionally operative to receive from the motion detector a tracking of a second body motion interacting with the second ball at the set position; and
   a communications device; and
a second subsystem with a communication link to the first subsystem, the second subsystem comprising:
   a display to show the image to a second person;
   a motion display to show a motion to the second person;
      a motion capture apparatus to capture a sporting motion by the second person, responsible to an image; and
      a comparison apparatus to capture the sporting motion by the first person with the sporting motion by the second person.

15. The system of claim 14, wherein the RF communication transmitter is embedded in the first golf ball.

16. The system of claim 14, the RF communication transmitter is embedded in the golf club.

* * * * *